(12) United States Patent  
Ito et al.

(10) Patent No.: US 8,343,701 B2  
(45) Date of Patent: *Jan. 1, 2013

(54) IMAGE FORMING MATERIAL

(75) Inventors: Yuka Ito, Ashigarakami-gun (JP); Minquan Tian, Ashigarakami-gun (JP); Suguru Nakaso, Ashigarakami-gun (JP); Shinji Hasegawa, Ashigarakami-gun (JP); Kazuhiko Hirokawa, Ashigarakami-gun (JP); Miho Watanabe, Ashigarakami-gun (JP); Takashi Matsubara, Ashigarakami-gun (JP); Makoto Furuki, Ashigarakami-gun (JP)

(73) Assignee: Fuji Xerox Co., Ltd., Tokyo (JP)

( * ) Notice: Subject to any disclaimer, the term of this patent is extended or adjusted under 35 U.S.C. 154(b) by 715 days.

This patent is subject to a terminal disclaimer.

(21) Appl. No.: 12/507,398

(22) Filed: Jul. 22, 2009

(65) Prior Publication Data

US 2010/0092885 A1  Apr. 15, 2010

(30) Foreign Application Priority Data

Oct. 10, 2008 (JP) .................. 2008-264157

(51) Int. Cl.
*G03G 9/09* (2006.01)
*C09D 11/02* (2006.01)
(52) U.S. Cl. ............. 430/105; 430/108.21; 544/231; 544/294
(58) Field of Classification Search .......... 544/249, 544/231, 294; 430/105, 108.21
See application file for complete search history.

(56) References Cited

U.S. PATENT DOCUMENTS 5,380,635 A  1/1995  Gomez et al.
(Continued)

FOREIGN PATENT DOCUMENTS

JP  09-090547 A  4/1997
(Continued)

OTHER PUBLICATIONS

U.S. Appl. No. 12/238,488, filed Sep. 26, 2008.

*Primary Examiner* — Hoa V Le
(74) *Attorney, Agent, or Firm* — Sughrue Mion, PLLC

(57) ABSTRACT

An image forming material includes a perimidine-substituted squarylium dye that has a structure represented by the following formula (I) and shows diffraction peaks at least at Bragg angles (2θ±0.2°) of 17.7°, 19.9°, 22.1°, 23.2° and 24.9° in its X-ray powder diffraction spectrum measured by irradiation with X rays generated from a Cu target with a wavelength of 1.5405 angstroms:

(I)

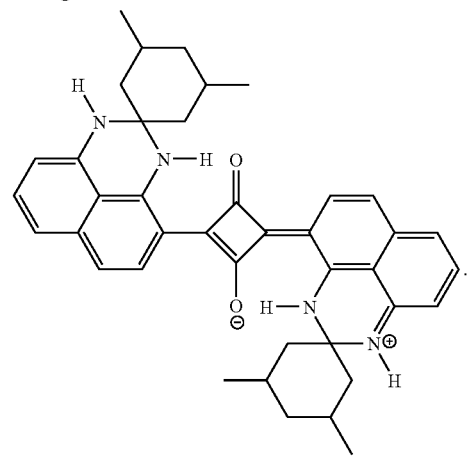

6 Claims, 6 Drawing Sheets

U.S. PATENT DOCUMENTS

| | | | |
|---|---|---|---|
| 5,935,755 A | 8/1999 | Kazmaier et al. | |
| 6,541,100 B1 | 4/2003 | Williams et al. | |
| 7,910,733 B2 * | 3/2011 | Tian et al. | 544/249 |
| 7,985,291 B2 * | 7/2011 | Hirokawa et al. | 106/287.25 |
| 8,017,291 B2 * | 9/2011 | Tian et al. | 430/108.1 |

FOREIGN PATENT DOCUMENTS

| | | |
|---|---|---|
| JP | 09-119867 A | 5/1997 |
| JP | 09-509503 T | 9/1997 |
| JP | 2000-207512 A | 7/2000 |
| JP | 2001-294785 A | 10/2001 |
| JP | 2002-278023 A | 9/2002 |

* cited by examiner

IMAGE FORMING MATERIAL

CROSS-REFERENCE TO RELATED APPLICATIONS

This application is based on and claims priority under 35 USC 119 from Japanese Patent Application No. 2008-264157 filed on Oct. 9, 2008.

BACKGROUND

1. Technical Field

The present invention relates to an image forming material.

2. Related Art

In recent years, techniques of drawing up documents or the like through the recording of invisible information lacking viewability under normal visual conditions have been received attention. These techniques are useful e.g. in management of security and embedding of Internet information and sound, and allow improvements in added value of the documents or the like.

As an example of a method for recording invisible information, there is the method of using an image forming material which has absorption in the near-infrared region of 750 to 1,000 nm and can be detected by a silicon-utilized light-sensitive element (CCD or the like) although it cannot be recognized by human eye.

SUMMARY

According to an aspect of the invention, there is provided an image forming material including a perimidine-substituted squarylium dye that has a structure represented by the following formula (I) and shows diffraction peaks at least at Bragg angles (2θ±0.2°) of 17.7°, 19.9°, 22.1°, 23.2° and 24.9° in its X-ray powder diffraction spectrum measured by irradiation with X rays generated from a Cu target with a wavelength of 1.5405 angstroms:

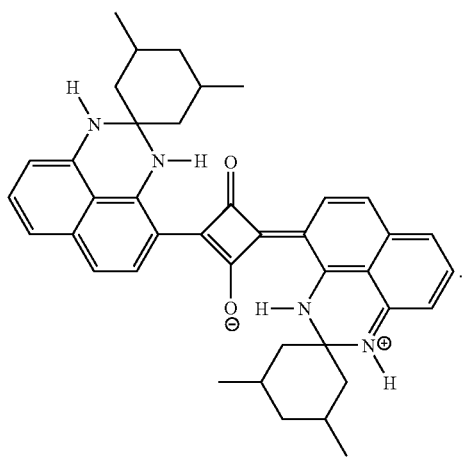

DETAILED DESCRIPTION

Figure 1:
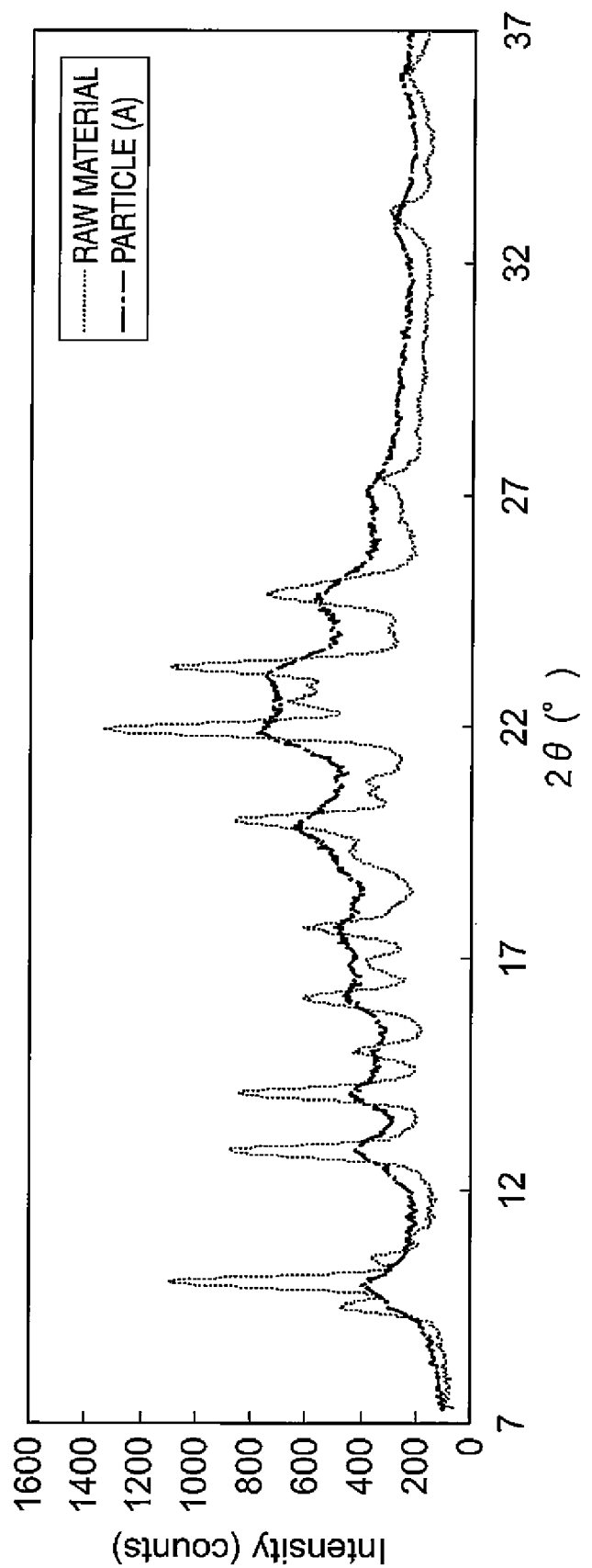
FIG. 1 is a graph showing the X-ray powder diffraction spectra of the Particles (A) and the raw material.

Exemplary embodiments suitable for the invention are described below in detail.

Each of the image forming materials according to exemplary embodiments of the invention contains a perimidine-substituted squarylium dye that has a structure represented by the following formula (I) and shows diffraction peaks at least at Bragg angles (2θ±0.2°) of 17.7°, 19.9°, 22.1°, 23.3° and 24.9° in its X-ray powder diffraction spectrum measured by irradiation with X rays generated from a Cu target with a wavelength of 1.5405 angstroms (hereafter referred to as "a perimidine-substituted squarylium dye relating to exemplary embodiments of the invention").

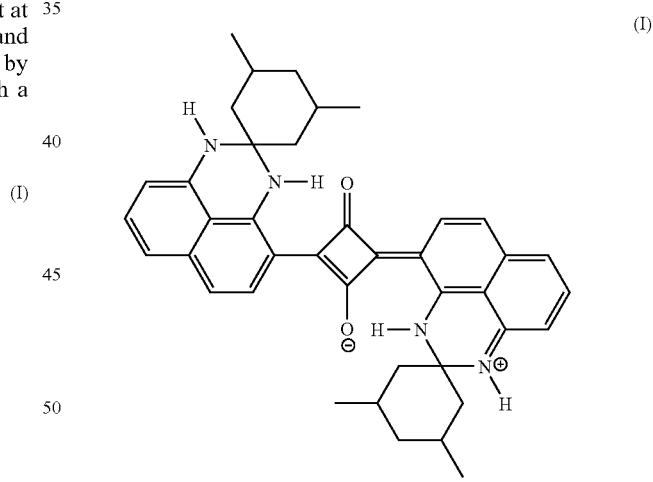

The perimidine-substituted squarylium dye of the structure represented by the formula (I) can be prepared according to e.g. the following reaction scheme:

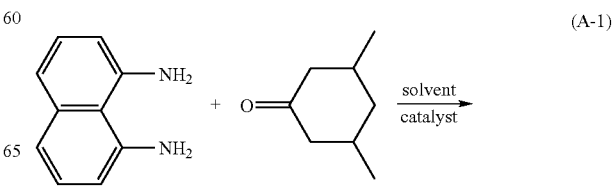

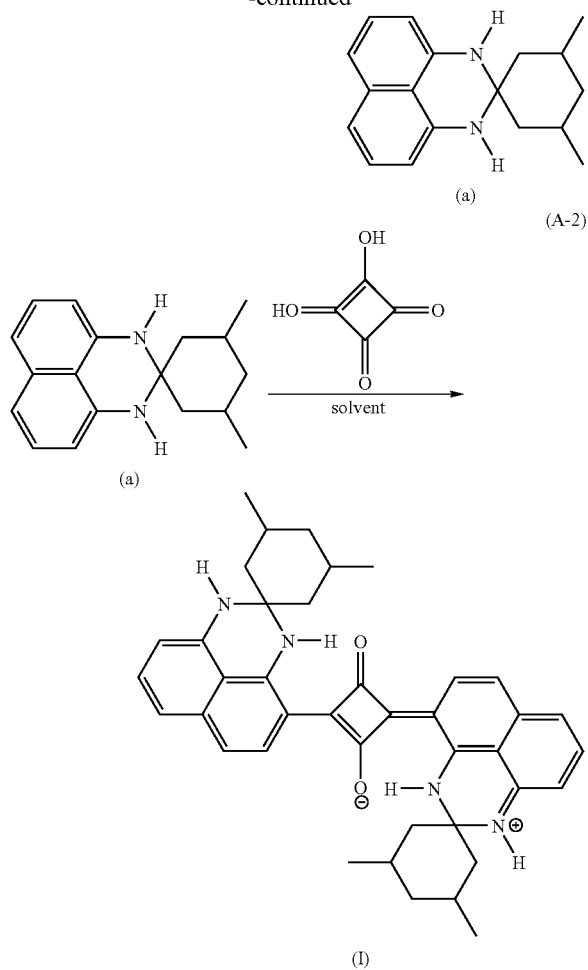

More specifically, the perimidine intermediate (a) can be prepared by allowing 1,8-diaminonaphthalene and 3,5-dimethylcyclohexanone to react with each other in the presence of a catalyst in a solvent under conditions of azeotropic reflux (Process (A-1)). Examples of a catalyst usable in Process (A-1) include p-toluenesulfonic acid monohydrate, benzenesulfonic acid monohydrate, 4-chlorobenzenesulfonic acid hydrate, pyridine-3-sulfonic acid, ethanesulfonic acid, sulfuric acid, nitric acid and acetic acid. And examples of a solvent usable in Process (A-1) include alcohol compounds and aromatic hydrocarbons. The perimidine intermediate (a) can be purified by high-speed column chromatography or recrystallization.

Next, the perimidine intermediate (a) is allowed to react with 3,4-dihydroxycyclobuta-3-ene-1,2-dione (referred to as "squaric acid" or "quadratic acid" too) in a solvent under conditions of azeotropic reflux, thereby preparing the perimidine-substituted squarylium dye represented by the formula (I) (Process (A-2)). It is preferred that Process (A-2) be performed in an atmosphere of nitrogen gas.

Examples of a solvent usable in Process (A-2) include alcohol compounds such as 1-propanol, 1-butanol and 1-pentanol, aromatic hydrocarbons such as benzene, toluene, xylene and monochlorobenzene, ethers such as tetrahydrofuran and dioxane, halogenated hydrocarbons such as chloroform, dichloroethane, trichloroethane and dichloropropane, and amides such as N,N-dimethylformamide and N,N-dimethylacetamide. Alcohol compounds may be used alone, but each of other solvents including aromatic hydrocarbons, ethers, halogenated hydrocarbons and amides is preferably used in a state of being mixed with an alcohol compound. Examples of a solvent preferably used include 1-propanol, 2-propanol, 1-butanol, 2-butanol, a solvent mixture of 1-propanol and benzene, a solvent mixture of 1-propanol and toluene, a solvent mixture of 1-propanol and N,N-dimethylformamide, a solvent mixture of 2-propanol and benzene, a solvent mixture of 2-propanol and toluene, a solvent mixture of 2-propanol and N,N-dimethylformamide, a solvent mixture of 1-butanol and benzene, a solvent mixture of 1-butanol and toluene, a solvent mixture of 1-butanol and N,N-dimethylformamide, a solvent mixture of 2-butanol and benzene, a solvent mixture of 2-butanol and toluene, and a solvent mixture of 2-butanol and N,N-dimethylformamide. When such a solvent mixture is used, it is preferable that the alcohol solvent concentration is at least 1% by volume, and more preferably from 5% to 75% by volume.

The mole ratio of the perimidine intermediate (a) to 3,4-dihydroxycyclobuta-3-ene-1,2-dione (the number of moles of the perimidine intermediate (a)/the number of moles of 3,4-dihydroxycyclobuta-3-ene-1,2-dione) in Process (A-2) is preferably from 1 to 4, and more preferably from 1.5 to 3. The mole ratios smaller than 1 tend to lower the yield of the perimidine-substituted squarylium dye represented by the formula (I), and the mole ratios greater than 4 tend to worsen the use effectiveness of the perimidine intermediate (a) and make it difficult to isolate and purify the perimidine-substituted squarylium dye represented by the formula (I).

In addition, the use of a dehydrating agent in Process (A-2) tends to reduce the reaction time and enhance the yield of the perimidine-substituted squarylium dye represented by the formula (I). The dehydrating agent used herein is not particularly limited so long as it reacts with neither the perimidine intermediate (a) nor 3,4-dihydroxycyclobuta-3-ene-1,2-dione, and suitable examples thereof include orthoformic acid esters such as trimethyl orthoformate, triethyl orthoformate, tripropyl orthoformate and tributyl orthoformate, a molecular sieve, and so on.

Although the reaction temperature in Process (A-2) varies depending on the kind of the solvent used, it is preferably 60° C. or higher, and more preferably 75° C. or higher. For example, when the solvent used is a solvent mixture of 1-butanol and toluene, the temperature of the reaction solution is preferably from 75° C. to 105° C.

In addition, the reaction time in Process (A-2) varies depending on the kind of the solvent used or the temperature of the reaction solution. For example, when the reaction is carried out under conditions that the solvent used is a solvent mixture of 1-butanol and toluene and the temperature of the reaction solution ranges from 90° C. to 105° C., the reaction time is preferably from 2 to 4 hours.

The perimidine-substituted squarylium dye produced in Process (A-2), which is represented by the formula (I), can be purified by washing with a solvent, high-performance column chromatography, or recrystallization.

When the perimidine-substituted squarylium dye obtained after the purification, which has the structure represented by the formula (I), is used as a color material of the image forming material, it is preferred that treatment for conversion into pigment be given to the dye. The treatment for conversion into pigment is apt to cause a change in crystal system of the dye. Therefore, it is appropriate that the method and conditions of treatment for conversion into pigment be chosen so that the resultant particles of the perimidine-substituted squarylium dye show diffraction peaks at least at Bragg angles (2θ±0.2°) of 17.7°, 19.9°, 22.1°, 23.2° and 24.9° in their X-ray powder diffraction spectrum measured by irradiation with X rays generated from a Cu target with a wavelength of 1.5405 angstroms.

A suitable example of the treatment method for conversion into pigment is the method of mixing the perimidine-substituted squarylium dye represented by the formula (I) and an aqueous solution of sodium dodecylbenzenesulfonate and giving treatment for conversion into pigment to the mixed solution. The concentration of the mixed solution may be adjusted by addition of water as required. Moreover, a bead milling apparatus is suitable as a device used in the treatment for conversion into pigment.

In the image forming material according to an exemplary embodiment of the invention, it is preferable that the perimidine-substituted squarylium dye relating to the exemplary embodiment of the invention is contained in the form of particles. Since the perimidine-substituted squarylium dye has great intermolecular interaction and particles thereof have high crystallinity, the image forming material can be given enhanced capability of developing infrared colors and light fastness by including the dye in the form of particles.

Particles of the perimidine-substituted squarylium dye relating to the exemplary embodiment of the invention can be formed e.g. as follows. The purified product after Process (A-2) is dissolved in tetrahydrofuran, the solution thus prepared is injected into ice-cold distilled water by means of a syringe or the like while stirring the water, thereby forming a precipitate, and the precipitate is suction filtered, washed with distilled water, and then subjected to vacuum drying. Thus, the particles can be obtained. At this time, the particle size of the precipitate can be controlled to the desired range by adjusting the concentration of the perimidine-substituted squarylium dye relating to the exemplary embodiment of the invention in the solution, the injection speed of the solution, the amount or temperature of the distilled water, the stirring speed, or/and so on. The median diameter d50 of particles of the perimidine-substituted squarylium dye relating to the exemplary embodiment of the invention is preferably from about 10 nm to about 300 nm, far preferably from about 20 nm to about 200 nm. When the median diameter d50 is smaller than 10 nm, light fastness of the dye particles tends to become low because the state of dye molecules in each particle approaches a monomolecular dispersed state and interaction among the dye molecules becomes small; while, when the median diameter d50 is greater than 300 nm, the dye particles tends have reduced capability of developing infrared colors because of increase in quantity of light scattered from the particle surfaces. Additionally, the foregoing processing for particle formation and median diameter control may be carried out either before or after the treatment for conversion into pigment so long as the perimidine-substituted squarylium dye after the processing shows diffraction peaks at least at Bragg angles (2θ±0.2°) of 8.9°, 17.1°, 18.4°, 22.6° and 24.2° in its X-ray powder diffraction spectrum measured by irradiation with X rays generated from a Cu target with a wavelength of 1.5405 angstroms.

In addition to the perimidine-substituted squarylium dye relating to exemplary embodiments of the inventions each of the image forming materials according to the exemplary embodiments of the invention can contain other ingredients as mentioned below. The content of the perimidine-substituted squarylium dye relating to each exemplary embodiment of the invention is preferably from about 0.05% by weight to about 3% by weight, and more preferably from about 0.1% by weight to about 2% by weight, based on the total weight of the image forming material.

The uses of the image forming material according to an exemplary embodiment of the invention are not particular limited, but preferable uses thereof are as electrophotographic toner, inkjet printer ink, ink for letterpress printing, offset printing, flexographic printing, gravure printing or silk-screen printing, and so on.

When it is electrophotographic toner, the image forming material according to an exemplary embodiment of the invention may be used by itself as a one-component developer, or may be used as a two-component developer in combination with a carrier. The carrier usable herein includes heretofore known ones. For instance, a resin-coated carrier having a resin coating on a core material can be used. In this resin coating, electrically conductive powder or the like may be dispersed.

In addition, when it is electrophotographic toner, the image forming material according to an exemplary embodiment of the invention can contain a binding resin. Examples of a binding resin usable herein include homopolymers or copolymers synthesized from a styrene monomer such as styrene or chlorostyrene, an olefin monomer such as ethylene, propylene, butylene or isoprene, a vinyl ester monomer such as vinyl acetate, vinyl propionate, vinyl benzoate or vinyl butyrate, an α-methylene aliphatic monocarboxylic acid ester monomer such as methyl acrylate, ethyl acrylate, butyl acrylate, dodecyl acrylate, octyl acrylate, phenyl acrylate, methyl methacrylate, ethyl methacrylate, butyl methacrylate or dodecyl methacrylate, a vinyl ether monomer such as vinyl methyl ether, vinyl ethyl ether or vinyl butyl ether, or/and a vinyl ketone monomer such as vinyl methyl ketone, vinyl hexyl ketone or vinyl isopropenyl ketone. Of these binding resins, especially typical ones include polystyrene, styrene-alkyl acrylate copolymers, styrene-alkyl methacrylate copolymers, a styrene-acrylonitrile copolymer, a styrene-butadiene copolymer, a styrene-maleic anhydride copolymer, polyethylene, polypropylene and the like. In addition, polyester, polyurethane, epoxy resin, silicone resin, polyamide, denatured rosin, paraffin wax and the like can also be used as binding resins.

When it is electrophotographic toner, the image forming material according to an exemplary embodiment of the invention can further contain a charge controlling agent, an offset inhibitor and so on as required. The charge controlling agent comes in two types, one for use with positive charge and the other for use with negative charge. For positive charge, a charge controlling agent such as a quaternary ammonium salt can be used. For negative charge, on the other hand, a charge controlling agent such as a metal complex of alkylsalicylic acid or a charge controlling agent of polar group-containing resin type can be used. Examples of an offset inhibitor usable therein include low-molecular-weight polyethylene and low-molecular-weight polypropylene.

When the image forming material according to an exemplary embodiment of the invention is electrophotographic toner, inorganic powdery particles or organic particles may be added as an external additive to the toner surface for the purposes of enhancing flowability and powder storage stability, controlling frictional electrification, improving transfer capability and cleaning capability, and so on. Examples of inorganic powdery particles include heretofore known ones such as silica, alumina, titania, calcium carbonate, magnesium carbonate, calcium phosphate and cerium oxide. Further, surface treatment of some known type may be given to those powdery inorganic particles in accordance with the intended purpose. On the other hand, examples of organic particles include emulsion polymerization agents containing as their constituents vinylidene fluoride, methyl methacrylate, a styrene-methyl methacrylate combination or the like, and soap-free polymers.

When it is inkjet printer ink, the image forming material according to an exemplary embodiment of the invention can take the form of aqueous ink in which water is contained. In order to prevent the ink from drying and enhance permeability of the ink, the image forming material according to an exemplary embodiment of the invention can further contain a water-soluble organic solvent. Examples of water used therein include ion exchange water, ultrafiltered water and deionized water. And examples of such an organic solvent include polyhydric alcohols such as ethylene glycol, diethylene glycol, polyethylene glycol and glycerin, N-alkylpyrrolidones, esters such as ethyl acetate and amyl acetate, lower alcohols such as methanol, ethanol, propanol and butanol, and glycol ethers such as ethylene oxide or propylene oxide adducts of methanol, butanol and phenol. Any one kind or kinds of organic solvent may be used. The organic solvent(s) to be used may be chosen as appropriate in consideration of hygroscopicity, moisture retention, solubility of the perimidine-substituted squarylium dye relating to the exemplary embodiment of the invention, permeability, viscosity of the ink, freezing temperature and so on. The organic solvent content in the inkjet printer ink is preferably from 1% to 60% by weight.

When it is inkjet printer ink, the image forming material according to an exemplary embodiment of the invention can contain additives hitherto known as ingredients of the ink in order to satisfy various requirements for inkjet printer systems. Examples of such additives include a pH adjusting agent, a resistivity adjusting agent, an antioxidant, an antiseptic, a fungicide and a metal blocking agent. Examples of a pH adjusting agent include alcoholamines, ammonium salts and metal hydroxides. Examples of a resistivity adjusting agent include organic salts and inorganic salts. Examples of a metal blocking agent include chelating agents.

When it is inkjet printer ink, the image forming material according to the invention can also contain a water-soluble resin, such as polyvinyl alcohol, polyvinyl pyrrolidone, carboxymethyl cellulose, styrene-acrylic acid resin or styrene-maleic acid resin, in such an amount as to cause neither clogging of jet nozzles nor change in discharge direction of the ink.

When it is ink for letterpress printing, offset printing, flexographic printing, gravure printing or silk-screen printing, the image forming material according to an exemplary embodiment of the invention can take the form of oil ink containing a polymer and an organic solvent. Examples of a polymer which can be contained therein include natural resins such as protein, rubber, cellulose, shellac, copal, starch and rosin, thermoplastic resins such as vinyl resin, acrylic resin, styrene resin, polyolefin resin and novolak phenol resin, and thermosetting resins such as resol-type phenol resin, urea resin, melamine resin, polyurethane resin, epoxy, and unsaturated polyester. Examples of an organic solvent which can be contained therein include those recited in the description of inkjet printer ink.

When it is ink for letterpress printing, offset printing, flexographic printing, gravure printing or silk-screen printing, the image forming material according to the invention can further contain additives, such as a plasticizer for enhancement of the elasticity and strength of printed film, a solvent for control of viscosity and enhancement of drying properties, a drying agent, a viscosity adjusting agent, a dispersing agent and various reacting agents.

Although the perimidine-substituted squarylium dye relating to every exemplary embodiment of the invention has outstanding light fastness, the image forming material according to each exemplary embodiment of the invention can further contain a stabilizer for the purpose of further enhancing light fastness in its uses. Since it is necessary for the stabilizer to receive energy from an organic near-infrared absorbing dye in an excited state, it is appropriate that the stabilizer have its absorption band at longer wavelengths than the absorption band which the near-infrared absorbing dye has. In addition, it is preferable that the stabilizer resists decomposition by singlet oxygen and has high compatibility with the perimidine-substituted squarylium dye relating to every exemplary embodiment of the invention. Examples of such a stabilizer include organometallic complex compounds. Such complex compounds suitable as the stabilizer include compounds represented by the following formula (V).

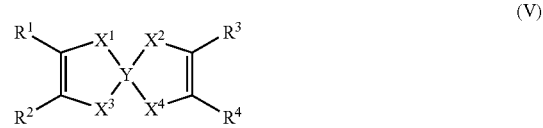

In the formula (V), $R^1$ to $R^4$ may be the same or different, and independently represent a substituted or unsubstituted phenyl group. When the phenyl group represented by any of $R^1$ to $R^4$ has a substituent, the substituent can be chosen from H, $NH_2$, OH, $N(C_hH_{2h+1})_2$, $OC_hH_{2h+1}$, $C_hH_{2h-1}$, $C_hH_{2h+1}$, $C_hH_{2h}OH$, $C_hH_{2h}OC_iH_{2i+1}$ or so on (wherein h represents an integer of 1 to 18, and i represents an integer of 1 to 6). And $X^1$ to $X^4$ may be the same or different, and independently represent O, S or Se, and Y represents a transition metal such as Ni, Co, Mn, Pd, Cu or Pt.

Of the compounds represented by the formula (V), the compound-represented by the following formula (VI) is preferred over the others.

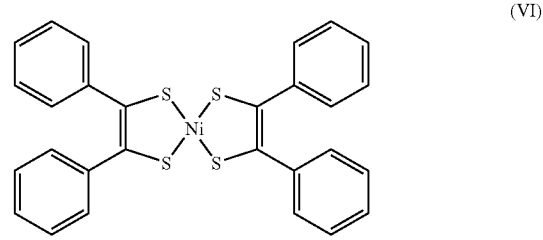

The suitable stabilizer concentration is of the order of ¹⁄₁₀ to 2 times as much as the content by weight of the perimidine-substituted squarylium dye relating to every exemplary embodiment of the invention.

The perimidine-substituted squarylium dye relating to every exemplary embodiment of the invention is a compound that has sufficiently low absorbance in the visible wavelength region of 400 nm to 750 nm, and sufficiently high absorbance in the near-infrared wavelength region of 750 nm to 1,000 nm. In addition, the perimidine-substituted squarylium dye relating to every exemplary embodiment of the invention has outstanding light fastness. Therefore, the image forming material according to each exemplary embodiment of the invention, in which the perimidine-substituted squarylium dye having such properties is contained, can achieve both invisibility of information written therewith and easy readout of the information, and further can ensure long-term stability of the recording material bearing invisible information recorded therewith.

It is preferred that the image forming material according to an exemplary embodiment of the invention satisfy the conditions given by the following expressions (II) and (III). By satisfying the expressions (II) and (III), the image forming material, irrespective of its color, comes to allow both invisibility of information written therewith and easy readout of the information, and also achievement of long-term reliability of a recording material bearing invisible information recorded therewith.

$$0 \leq \Delta E \leq 16 \quad \text{(II)}$$

$$(100-R) \geq 75 \quad \text{(III)}$$

ΔE in the expression (II) represents a color difference in the CIE1976 L*a*b* color specification system, which is given by the following expression (IV);

$$\Delta E = \sqrt{(L_1-L_2)^2+(a_1-a_2)^2+(b_1-b_2)^2} \quad \text{(IV)}$$

(wherein $L_1$, $a_1$ and $b_1$ represent values of L, a and b, respectively, of a recording material surface on which no image is formed yet, and $L_2$, $a_2$ and $b_2$ represent values of L, a, and b, respectively, in a formed image part of the recording material surface where a fixed image is formed by use of the image forming material which adheres to the surface in an adhesion amount of 4 g/m$^2$), and R (unit: %) in the expression (III) represents reflectance of infrared radiation with the wavelength of 850 nm on the formed image part.

Values $L_1$, $a_1$, $b_1$, $L_2$, $a_2$, and $b_2$ can be determined by means of a reflection spectrodensitometer. The values $L_1$, $a_1$, $b_1$, $L_2$, $a_2$ and $b_2$ in the invention are values measured by using x-rite 939 made by X-Rite, Inc. as the reflection spectrodensitometer.

Invisible information recorded by use of the image forming material according to an exemplary embodiment of the invention allows very easy and highly sensitive readout through the combined use of e.g. a semiconductor laser or light-emitting diode as a light source for optical reading, which generates radiation with any of the wavelengths ranging from 750 nm to 1,000 nm, and an off-the-shelf photoreceptor having high spectral sensitivities to near-infrared rays. Examples of such a photoreceptor include silicon-based photoreceptors (such as CCDs).

EXAMPLES

The invention will now be illustrated more concretely by reference to an Example and Comparative Examples, but the following Example should not be construed as limiting the scope of the invention in any way.

Example 1

<Preparation of Perimidine-Substituted Squarylium Dye: Two-Step Synthesis>

A mixed solution prepared from 4.843 g (98%, 30.0 mmol) of 1,8-diaminonaphthalene, 3.886 g (98%, 30.2 mmol) of 3,5-dimethylcyclohexanone, 10 mg (0.053 mmol) of p-toluenesulfonic acid monohydrate and 45 ml of toluene is heated with stirring in an atmosphere of nitrogen gas and refluxed for 5 hours. And the water produced during the reaction is removed by component distillation. After the conclusion of the reaction, a dark brown solid obtained by distilling the toluene from the reaction solution is extracted with acetone, purified by recrystallization from a mixed solvent of acetone and ethanol, and further dried. Thus, 7.48 g of a brown solid is obtained (in 93.6% yield). Results of $^1$H-NMR spectrum (in CD$_3$Cl) analysis performed on the thus obtained brown solid are shown below.

$^1$H-NMR spectrum (in CD$_3$Cl): δ=7.25, 7.23, 7.22, 7.20, 7.17, 7.15 (m, 4H, H$_{arom}$); 6.54 (d×d, J$_1$=23.05 Hz, J$_2$=7.19 Hz, 2H, H$_{arom}$); 4.62 (br s, 2H, 2×NH); 2.11 (d, J=12.68 Hz, 2H, CH$_2$); 1.75, 1.71, 1.70, 1.69, 1.67, 1.66 (m, 3H, 2×CH, CH$_2$); 1.03 (t, J=12.68 Hz, 2H, CH$_2$); 0.89 (d, J=6.34 Hz, 6H, 2×CH$_3$); 0.63 (d, J=11.7 Hz, 1H, CH$_2$)

A mixed solution prepared from 4.69 g (17.6 mmol) of the brown solid obtained and 913 mg (8.0 mmol) of 3,4-dihydroxycyclobuta-3-ene-1,2-dione, 40 ml of n-butanol and 60 ml of toluene is heated with stirring in an atmosphere of nitrogen gas and refluxed for 3 hours, thereby undergoing reaction. The water produced during the reaction is removed by component distillation. After the conclusion of the reaction, most of the solvents are distilleds away in the atmosphere of nitrogen gas, and 120 ml of hexane is added to the resultant reaction mixture while stirring. The thus formed blackish brown precipitate is suction filtered, washed with hexane, and dried, thereby yielding a blackish blue solid. This solid is washed with successive ethanol, acetone, 60% aqueous ethanol solution, ethanol and acetone. Thus, 4.30 g of the desired compound (blackish blue solid) is obtained, a 88% yield.

Figure 3:
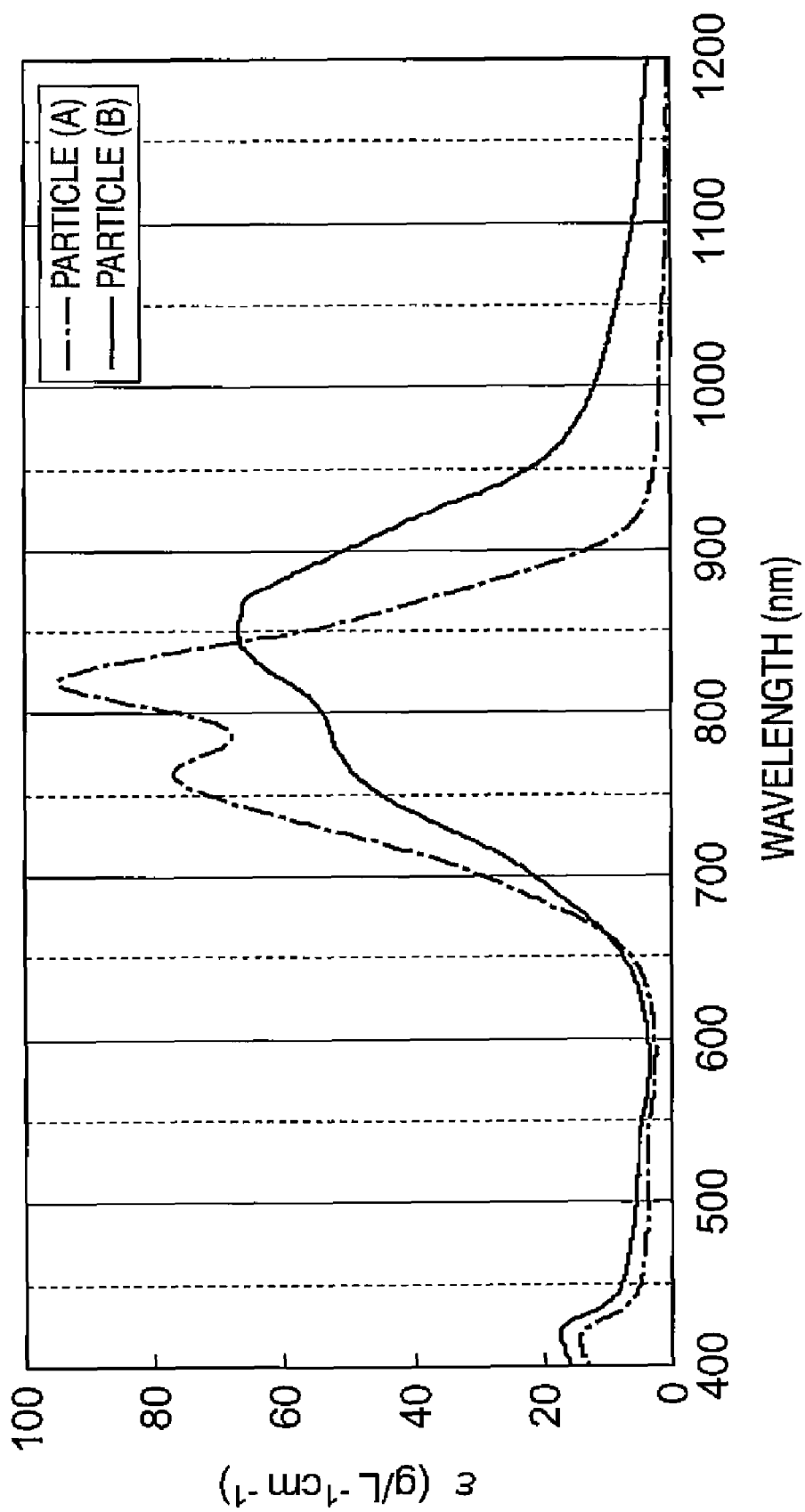
FIG. 3 is a graph showing the visible near-infrared absorption spectra of the slurry prepared by using the Particles (A) and the slurry prepared by using the Particles (B)

The dye compound thus obtained is identified by its infrared absorption spectrum (KBr tablet method), $^1$H-NMR spectrum (in DMSO-d$_6$) and FD-MS measurements, elemental analysis, and spectroscopies including visible near-infrared absorption spectroscopy. Data for identification are shown below. In addition, a visible near-infrared absorption spectrum of the dye compound obtained is shown in FIG. 3. By these experimental results for identification, the dye compound obtained is ascertained to be the perimidine-substituted squarylium dye represented by the formula (I).

Infrared Absorption Spectrum (KBr tablet method):

$v_{max}$ (cm$^{-1}$)=3487, 3429, 3336 (NH), 3053 (=C—H), 2947 (CH$_3$), 2914, 2902 (CH$_2$), 2864 (CH$_3$), 2360, 1618, 1599, 1558, 1541 (C=C ring), 1450, 1421, 1363 (CH$_3$, CH$_2$), 1315, 1223, 1201 (C—N), 1163, 1119 (C—O$^-$), 941, 924, 822, 783, 715 cm$^{-1}$ $^1$H-NMR Spectrum (in DMSO-d$_6$):

δ=10.52 (m, 2H, NH); 7.80, 7.78 (d, 2H, H$_{arom}$); 7.35, 7.33 (m, 2H, H$_{arom}$); 7.25 (m, 2H, NH); 6.82, 6.80, 6.78 (m, 4H, H$_{arom}$); 6.74, 6.72, 6.52, 6.50 (m, 2H, H$_{arom}$); 2.17 (m, 5H, CH$_2$); 1.91 (m, 3H, CH$_2$); 1.71 (m, 2H, CH, CH$_2$); 1.15, 1.12 (m, 4H, CH$_2$); 0.92, 0.91 (m, 12H, 4×CH$_3$); 0.66 (m, 2H, CH$_2$)

Mass Spectrum (FD):

m/z=610 (M$^+$, 100%), 611 (M$^+$+1, 47.5%)

Elemental Analysis:

C: 78.6% (measured), 78.66% (calcd.)
H: 6.96% (measured), 6.93% (calcd.)
N: 9.02% (measured), 9.17% (calcd.)
O: 5.42% (measured), 5.24% (calcd.)

Visible Near-Infrared Absorption Spectrum (FIG. 3):

$\lambda_{max}$=809 nm (in tetrahydrofuran solution)
$\epsilon_{max}$=1.68×10$^5$ M$^{-1}$cm$^{-1}$ (in tetrahydrofuran solution)

<Treatment for Conversion into Pigment>

Then, 51 g of the perimidine-substituted squarylium dye obtained, 25 g of a 12% aqueous solution of sodium dodecylbenzenesulfonate and 425 g of water are charged into bead milling apparatus (MINICER, made by Ashizawa Finetech Ltd.), and the milling operation using 485 g of 0.1-mm-φ beads is performed for 3 hours at a peripheral speed of 12 m/s.

When the perimidine-substituted squarylium dye is collected (hereafter referred to as "Particles (A)") and examined for particle size distribution, the median diameter thereof is found to be 65.9 nm.

Comparative Example 1

Perimidine-substituted squarylium dye particles not given the treatment for conversion into pigment in Example 1 (hereafter referred to as "raw material") in an amount of 50 mg, together with 1 mL of tetrahydrofuran (THF) and 10 g of zirconia beads of 1-mm diameter, are placed in a vessel for ball mill use and subjected to 1-hour milling. Then, water is added to the vessel for ball mill use, and the thus processed perimidine-substituted squarylium dye particles (hereafter referred to as "Particles (B)") are collected through filtration with a 50-nm filter.

<<X-Ray Powder Diffraction Measurement>>

Figure 2:
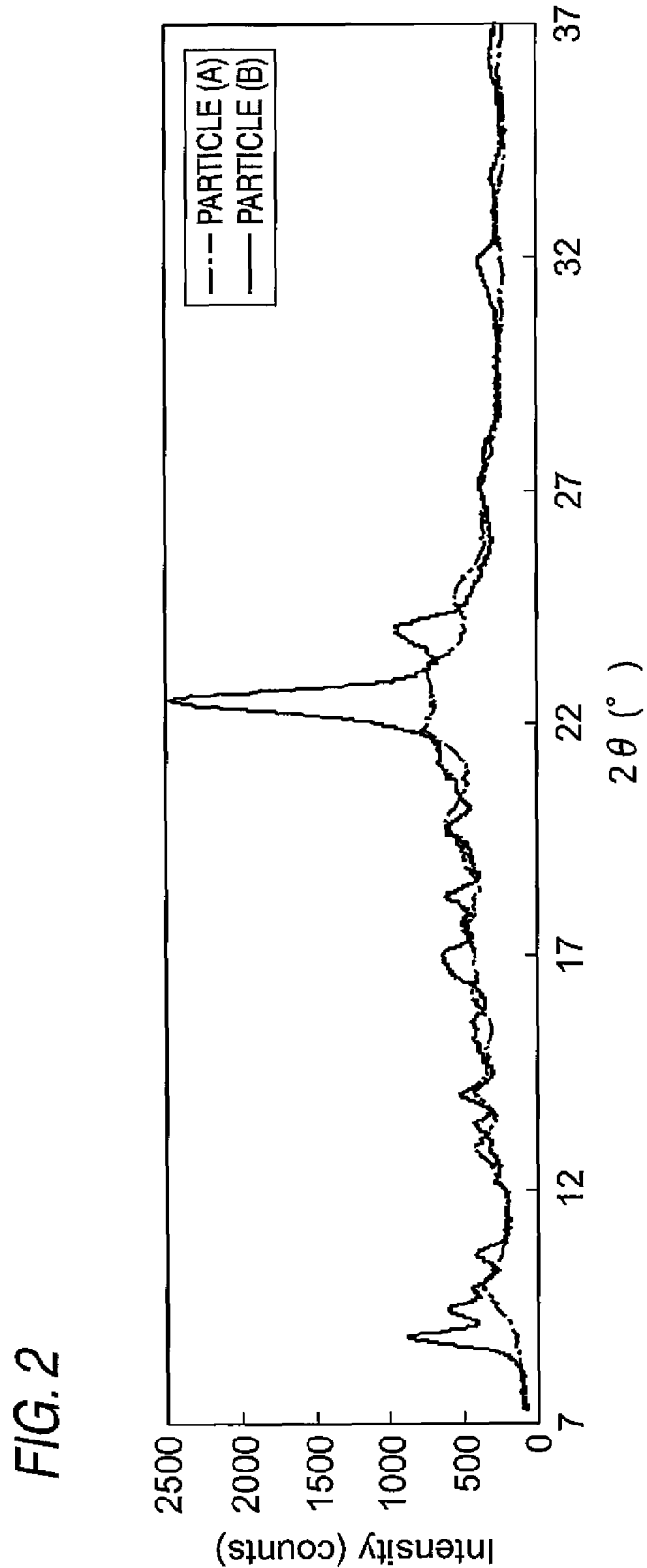
FIG. 2 is a graph showing the X-ray powder diffraction spectra of the Particles (A) and the Particles (B)

X-ray powder diffraction measurements by irradiation with X rays of λ=1.5405 angstroms generated from a Cu target and by means of an X-ray diffraction instrument (D8 DISCOVER, made by Bruker AXS K. K.) are made on the perimidine-substituted squarylium dye particles which do not undergo the treatment for conversion into pigment in Example 1 (raw material), Particles (A), and Particles (B), respectively. X-ray powder diffraction spectra obtained are shown in FIG. 1 and FIG. 2. As seen from FIG. 1, the spectrum of the Particles (A) indicates diffraction peaks, expressed in terms of Bragg angle (2θ±2°), at 22.1°, 23.2°, 19.9°, 24.9° and 17.7° in decreasing order of intensity, and this measurement result proves that the Particles (A) belong to the same crystal system as the raw material does. On the other hand, the spectrum of the Particles (B), as seen from FIG. 2, indicates diffraction peaks, expressed in terms of Bragg angle (2θ±2°), at 22.6°, 24.2°, 8.9°, 17.1° and 18.4° in decreasing order of intensity, and this measurement result proves that the crystal system of the Particles (B) is different from the crystal system to which the raw material and the Particles (A) belong.

<<Visible Near-Infrared Absorption Spectrum Measurement>>

The Particles (A) or the Particles (B) in an amount of 9.2 mg, together with 46 μl of a 12% aqueous solution of sodium dodecylbenzenesulfonate and 5.52 ml of distilled water, are subjected to ultrasonic dispersion (ultrasonic power: 4-5W, use of a ¼-inch horn, irradiation time: 30 minutes), and thereby made into slurry. The concentration of sample particles in the slurry is 0.165 wt %. Visible near-infrared spectra of the two kinds of slurry thus prepared are shown in FIG. 3. As seen from FIG. 3, the spectrum of the slurry of Particles (A) is different in absorption pattern from that of the slurry of Particles (B).

From the results mentioned above, it is thought that the Particles (A) can be ground and still remain unchanged, in the same crystal system as the raw material, since they are prepared by the bead milling of the raw material mixed with an aqueous solution of sodium dodecylbenzenesulfonate and water; as a consequence, color developing capability as seen in the spectrum of their slurry can be enhanced.

<<Infrared Output Spectrum Measured with PEN Device>>

Figure 4:
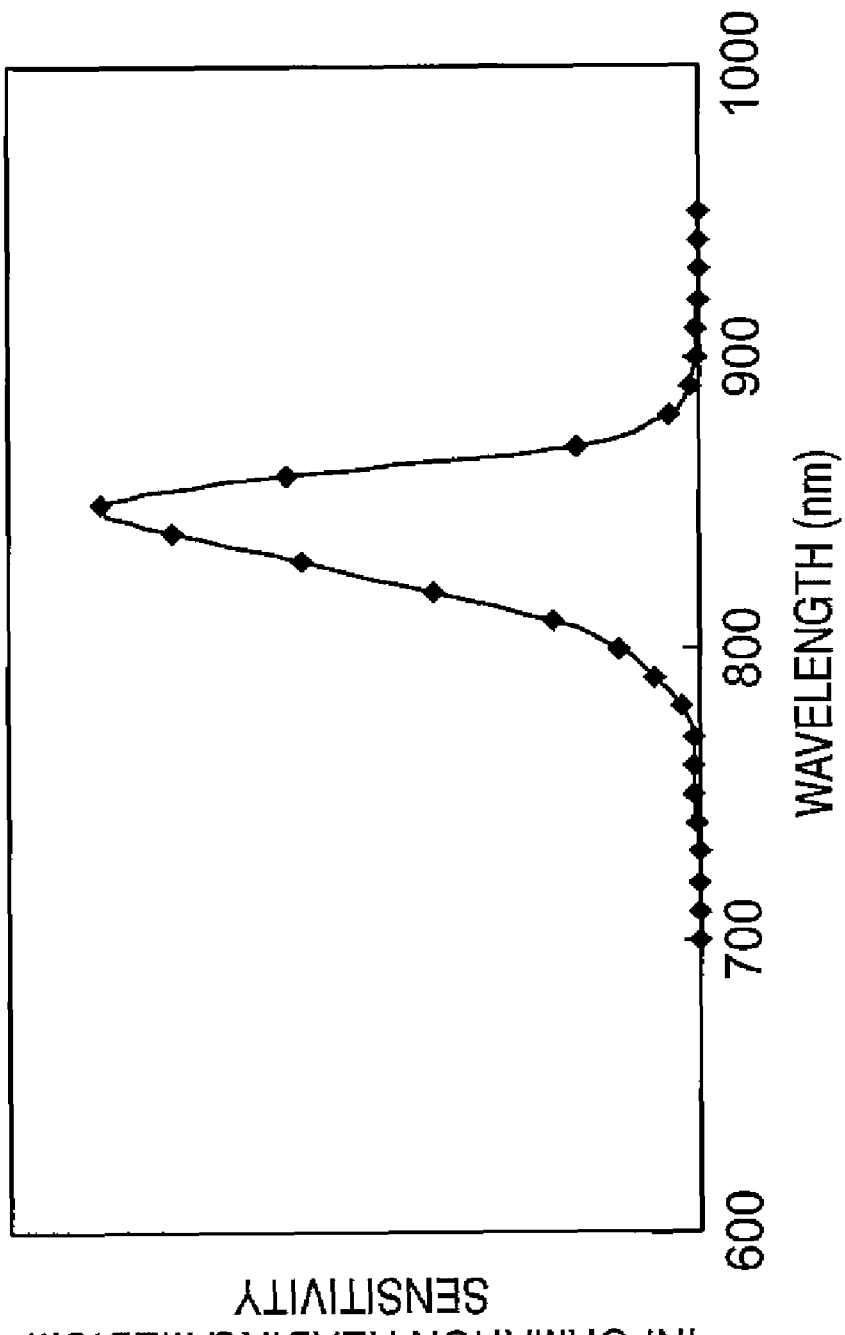
FIG. 4 is a graph showing the PEN device infrared output spectrum concerning the Particles (A)

An infrared output spectrum of a PEN device (emission spectrum of the PEN LED) is shown in FIG. 4.

<<Readability Evaluation>>

Toner samples are prepared using the Particles (A) and the Particles (B), respectively. More specifically, simulating toners containing the Particles (A) (Crystal A) or the Particles (B) (Crystal B) as color materials, samples for evaluation purposes are prepared by performing the following steps, and reflection spectra thereof are measured.

To begin with, the slurry prepared in the foregoing manner in which Crystal A or Crystal B is contained, and an aqueous dispersion of resin are mixed, and this liquid is made into a slurry through dispersion processing by means of ULTRA-TURRAX (made by IKA Japan). An aluminum sulfate flocculant is further added to this mixed slurry, and they are mixed together by agitation. Thus, a dispersion liquid simulating a toner is prepared.

Figure 5:
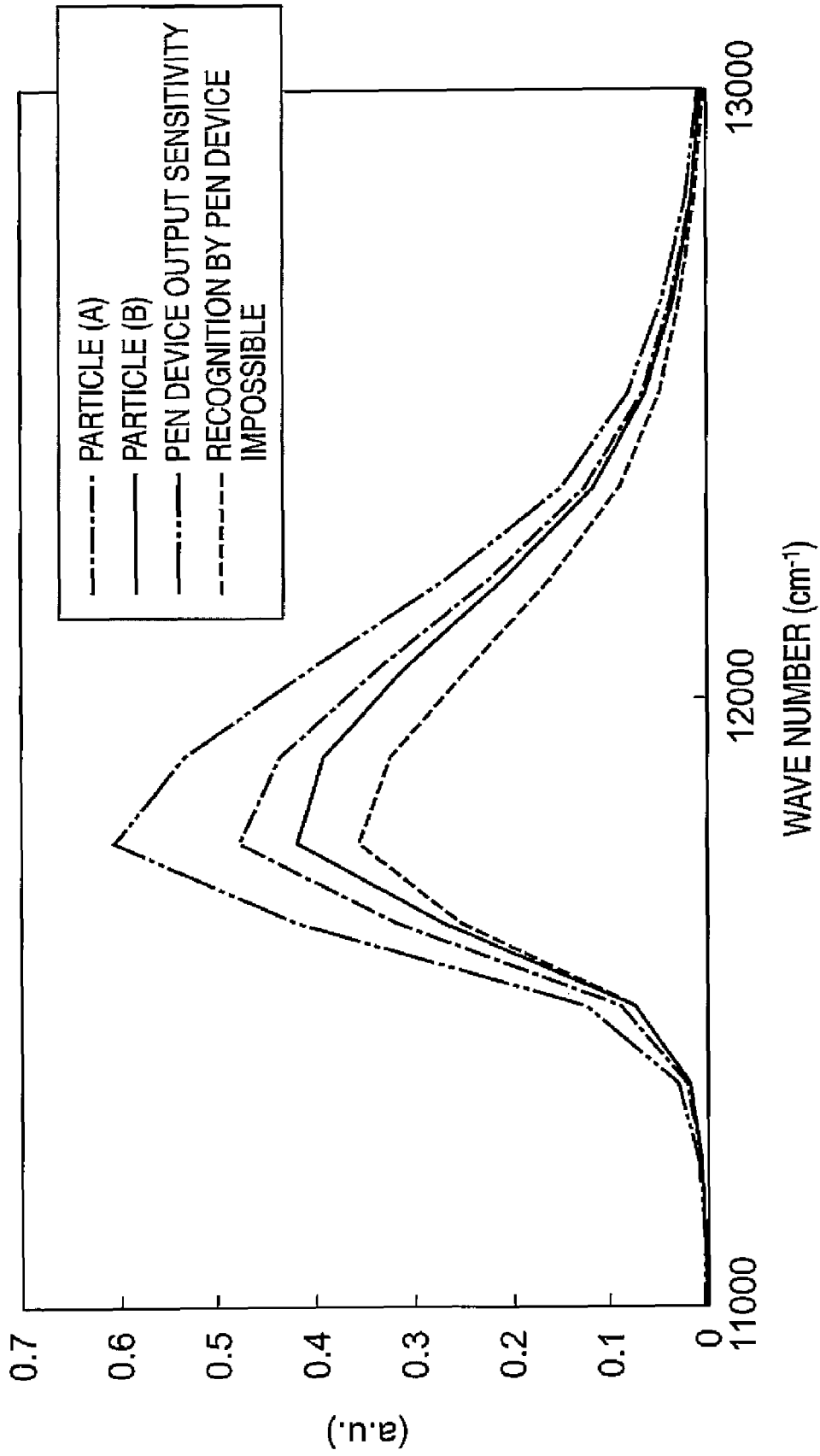
FIG. 5 is a graph showing the relationship of wave numbers to the product of output sensitivity of emission spectrum of the PEN device multiplied by absorbance (1-reflectance) of the toner concerning the Particles (A) and the Particles (B)

Each of the thus prepared simulated-toner dispersion liquids is filtered and leaves a deposit on filter paper (GSWP04700, trade name, a product of Millipore Corporation, pore size: 220 nm), and then the deposit is dried in the air. Further, the dried deposit is subjected to thermocompression bonding at 120° C. to form resin film on the filter paper. Thus, samples for evaluation purposes are obtained. Each sample is equivalent to toner containing the color material and the binding resin printed over the entire surface of a sheet of paper. Additionally, each sample prepared for evaluation purposes is made to have a resin film in which the total amount of the color material and the resin (the mass of total solids) is fixed to 4.0 g/m$^2$ as expressed in gram number per square meter (TMA) by controlling the amounts of the color material and the resin which are mixed together in preparing the mixture, and the amount of the color material per unit area (PMA) at this time is controlled to 0.04 g/m$^2$ (equivalent to color material content of 1% by mass). Next, the absorbance (1-reflectance) evaluation and the readability evaluation based on output sensitivity of the emission spectrum of the PEN device are performed on each toner obtained. Each graph in FIG. 5 shows a relationship between the wave number and the product of the output sensitivity of the emission spectrum of the PEN device and the absorbance (1-reflectance) of each toner. The integral of each graph shown in FIG. 5 is an index of the PEN readability of each toner, and a larger integral allows easier recognition by the PEN device. As can be seen from FIG. 5, the toner using the Particles (A) offers higher readability than the toner using the Particles (B).

<Life Expectancy Graph>

Figure 6:
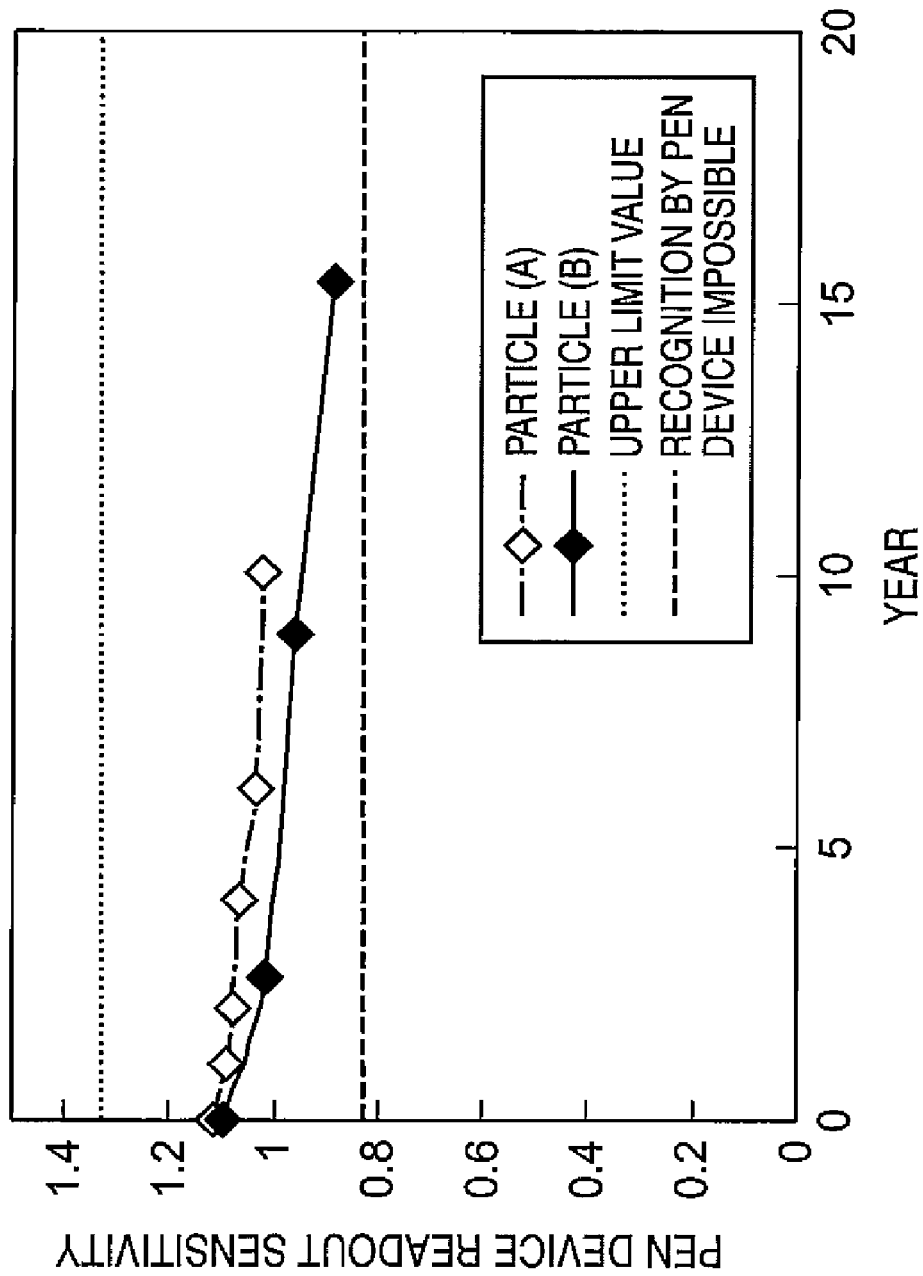
FIG. 6 is a graph showing the relationship of light irradiation time to PEN device readout sensitivity, which is obtained from accelerated fluorescent-lamp irradiation tests performed on the toner samples prepared using the Particles (A) and the Particles (B).

Accelerated fluorescent-lamp irradiation testing is performed on each of the toner samples prepared using the Particles (A) and the Particles (B), respectively, the irradiation time therein is converted into an irradiation time in office environment, and the life time of each toner is taken to be the life expectancy of the PEN device for XEPHY. FIG. 6 graphically displays the relationships between the light irradiation time and the readout sensitivity of the PEN device, and indicates the color fading property of toner prints. Additionally, the upper limit readout sensitivity of the PEN device and the sensitivity at which recognition by the PEN device is impossible are also shown in FIG. 6. As can be seen from FIG. 6, the Particles (A) offer a longer life time than the Particles (B).

<Colorimetric Evaluation>

A mixture of 40.4 μL of the slurry of Particles (A) or Particles (B) (0.165 wt % sample concentration), 15 μL of a 40 wt % latex (copolymer of styrene and n-butyl acrylate) solution and 5 g of distilled water is subjected to dispersion processing by use of ULTRA-TURRAX, thereby preparing mixed slurry. To the mixed slurry thus obtained, a polyaluminum chloride (PAC) flocculant is added to prepare a dispersion liquid simulating toner. This simulated-toner dispersion liquid is passed through a 220-nm filter, and a deposit left on the filter is air-dried and further subjected to thermocompression bonding (120° C., mode 1), thereby making a latex patch for evaluation, which meets conditions of TMA=4.5 g/m$^2$ and the amount of pigment per unit area PMA=0.045 g/m$^2$ (equivalent to 1 wt %)). The thus obtained latex patch (coated paper) is adopted as a sample, measurements with a reflection spectrodensitometer (x-rite 939, made by X-Rite, Incorporated) are made on the sample, and ΔE in the expression (II) and R in the expression (III) are determined from results of the measurements. Evaluation results of the coated paper samples are shown in Table 1. The evaluation rankings for "readability" and "invisibility" in Table 1 are defined as follows (hereafter the same criteria are applied).

<Readability>
A: Initial reflectance R(%) at 850 nm≦22
B: 22≦Initial reflectance R(%) at 850 nm≦30
C: Initial reflectance R(%) at 850 nm≦30

<Invisibility>
A: 0≦ΔE≦7
B: 7≦ΔE≦16
C: ΔE>16

Comparative Example 2

Colorimetric evaluations are performed on a vanadyl naphthalocyanine dye currently in use (hereafter referred to as "VONPc") as in the cases using the Particles (A) and the Particles (B). Results obtained are shown in Table 1.

Comparative Example 3

A dye compound-represented by the following formula (VII) is subjected to microparticulation processing in accordance with the following method.

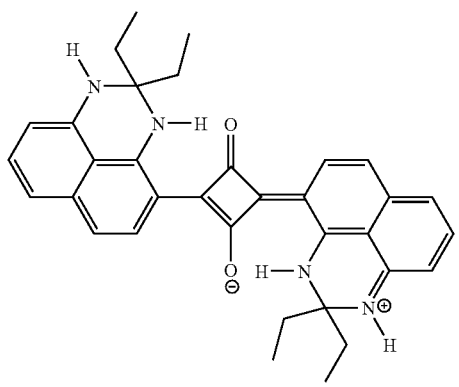

(VII)

<Reprecipitation Method>

The dye compound represented by the formula (VII) in an amount of 40 mg is dissolved in 30 mL of THF, and the solution obtained is injected all at once into 2,000 mL of ice-cold distilled water by means of a micro-syringe, thereby performing reprecipitation. After a lapse of several minutes, the mixed solution is restored to room temperature and the precipitate is filtered off by use of a 50-nm filter, washed with distilled water, and then vacuum-dried. Thus, the reprecipitated dye compound (hereafter referred to as "Particles (C)") is collected. The particle size of Particles (C) is about 90 nm as expressed in terms of median diameter d50. When X-ray powder diffraction of Particles (C), as is the case with ISQ-10(A), is measured by irradiation with X rays of X=1.5405 angstroms generated from a Cu target, almost no peaks of crystalline origin are noticed in its spectrum, indicating that the Particles (C) obtained by the reprecipitation method is amorphous.

Comparative Example 4

<Reprecipitation Method+Milling Method>

In a vessel for ball mill use, 40 mg of Particles (C) obtained by the reprecipitation method in Comparative Example 3, 5 ml of hexane and 10 g of agate beads having a diameter of 1 mm are placed, and subjected to 8-hour milling. Water is added to the vessel for ball mill use, and the dye compound thus microparticularized (hereafter referred to as "Particles (D) particles") is collected by filtration with a 50-nm filter. The size of the Particles (D) particles is about 90 nm as expressed in terms of median diameter d50. An X-ray powder diffraction spectrum of the Particles (D) particles measured, as with the case of the Particles (A) in Example 1, by irradiation with X rays of λ=1.5405 angstroms generated from a Cu target is shown in FIG. 8. In this X-ray powder diffraction spectrum, the presence of diffraction peaks are recognized at least at Bragg angles (2θ±0.2°) of 11.9°, 13.1°, 15.4°, 19.0°, 20.4°, 23.0°, 23.9°, 24.6° and 26.4°. As is evident from this result, the Particles (D) obtained has high crystallinity.

Colorimetric evaluations are performed on Particles (C) obtained in Comparative Example 3 and Particles (D) obtained in Comparative Example 4 as in the cases of the Particles (A) and the Particles (B). Results obtained are shown in Table 1.

TABLE 1

| | Sample | Initial reflectance R(%) at 850 nm | ΔE | Readability | Invisibility |
|---|---|---|---|---|---|
| Example 1 | Particles (A) | 21.34 | 5.6 | A | A |
| Comparative Example 1 | Particles (B) | 28.29 | 6.1 | B | A |
| Comparative Example 2 | VONPc | 24.76 | 32.4 | B | C |
| Comparative Example 3 | Particles (C) | 51.73 | 9.02 | C | B |
| Comparative Example 4 | Particles (D) | 60.72 | 8.9 | C | B |

What is claimed is:

1. An image forming material comprising:
a perimidine-substituted squarylium dye that has a structure represented by the following formula (I) and shows diffraction peaks at least at Bragg angles (2θ±0.2°) of 17.7°, 19.9°, 22.1°, 23.2° and 24.9° in its X-ray powder diffraction spectrum measured by irradiation with X rays generated from a Cu target with a wavelength of 1.5405 angstroms:

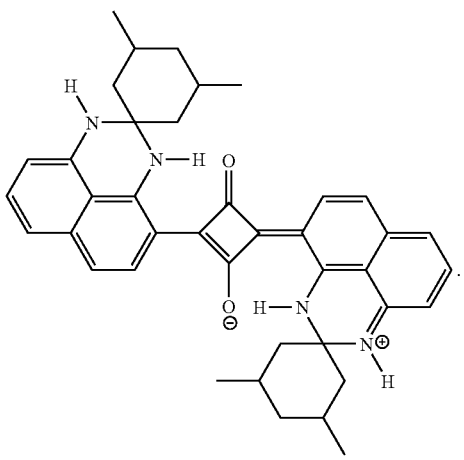

(I)

2. The image forming material as described in claim 1, wherein
the perimidine-substituted squarylium dye is obtained by mixing a perimidine-substituted squarylium dye having the structure represented by the formula (I) and a solution of sodium dodecylbenzenesulfonate and then subjecting the mixed solution to a treatment for conversion into pigment.

3. The image forming material as described in claim 1, wherein
the perimidine-substituted squarylium dye is in a state of a crystalline particle having a median diameter d50 of about 10 nm to about 300 nm.

4. The image forming material as described in claim 1, wherein the perimidine-substituted squarylium dye is contained in an amount of about 0.05% by weight to about 3% by weight.

5. The image forming material as described in claim 1, which is an electrophotographic toner; an inkjet printer ink; or an ink for letterpress printing, offset printing, flexographic printing, gravure printing or silk-screen printing.

6. The image forming material as described in claim 1, which satisfies conditions represented by the following expressions (II) and (III):

$$0 \leq \Delta E \leq 16 \quad \text{(II)}$$

$$(100-R) \geq 75 \quad \text{(III)}$$

wherein
in the expression (II), $\Delta E$ represents a color difference in the CIE1976 L*a*b* color specification system, which is given by the following expression (IV):

$$\Delta E = \sqrt{(L_1-L_2)+(a_1-a_2)^2+(b_1-b_2)^2} \quad \text{(IV)}$$

wherein
in the expression (IV), $L_1$, $a_1$ and $b_1$ represent values of L, a and b, respectively, of a recording material surface, on which no image is formed yet, and
$L_2$, $a_2$ and $b_2$ represent values of L, a and b, respectively, in a formed image part of the recording material surface, where a fixed image having an adhered amount is 4 g/m² is formed by use of the image forming material, and
in the formula (III), R (unit: %) represents a reflectance of infrared radiation with the wavelength of 850 nm on the formed image part.

* * * * *